United States Patent [19]
Jinotti

[11] Patent Number: 5,255,672
[45] Date of Patent: Oct. 26, 1993

[54] DUAL-PURPOSE CATHETER ASSEMBLY

[76] Inventor: Walter J. Jinotti, 10 Scott St., New Brunswick, N.J. 08903

[21] Appl. No.: 741,571
[22] Filed: Aug. 7, 1991
[51] Int. Cl.[5] .................................. A61M 16/00
[52] U.S. Cl. ..................... 128/200.26; 128/207.14; 128/207.16
[58] Field of Search ................ 128/200.26, 207.14, 128/207.15, 207.16

[56] References Cited

U.S. PATENT DOCUMENTS

| | | | |
|---|---|---|---|
| 4,036,210 | 7/1977 | Campbell et al. | 128/207.16 |
| 4,595,005 | 6/1986 | Jinotti | 128/207.14 |
| 4,674,496 | 6/1987 | Svadjian et al. | 128/207.16 |
| 5,088,486 | 2/1992 | Jinotti | 128/207.14 |

Primary Examiner—Edgar S. Burr
Assistant Examiner—Aaron J. Lewis
Attorney, Agent, or Firm—Robert A. Green

[57] ABSTRACT

A dual-purpose catheter assembly including a valve having two outlet tubes for providing oxygen and suction to a patient and a coupling manifold adapter coupled to the two outlet tubes and having a single small diameter lumen coupled to a pediatric patient.

15 Claims, 4 Drawing Sheets

DUAL-PURPOSE CATHETER ASSEMBLY

BACKGROUND OF THE INVENTION

A new type of valve for a dual purpose catheter has been devised by the present inventor and this valve has been described for use primarily with adults. However, there is often a need for applying suction and oxygen to an infant and the present invention relates to such use.

DESCRIPTION OF THE DRAWINGS

FIG. 3 is a front elevational view of the control valve shown in FIG. 1;

FIG. 4 is a rear elevational view of the control valve of FIG. 1;

DESCRIPTION OF THE INVENTION

Figure 1:
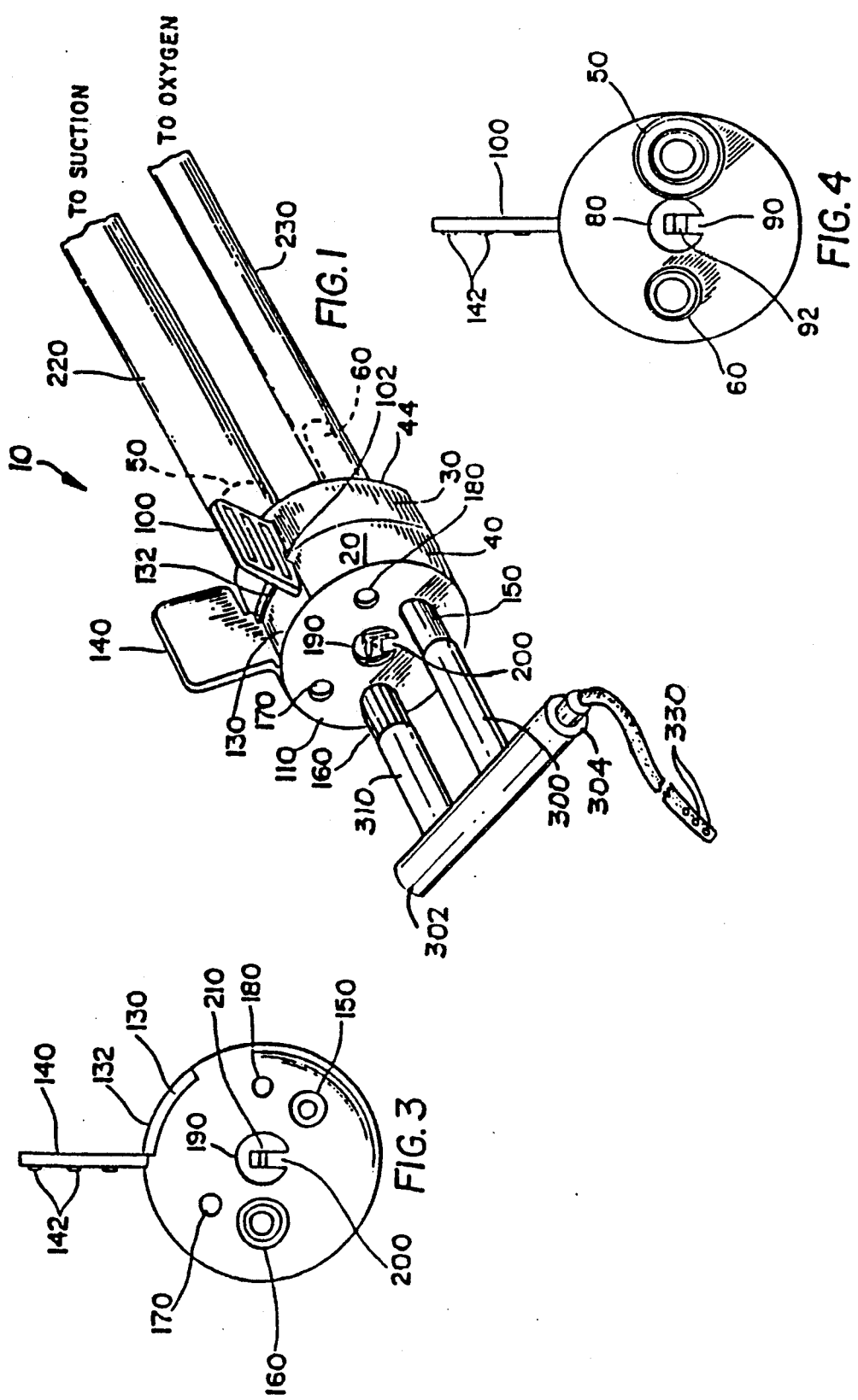
FIG. 1 is a perspective view of a dual-purpose catheter system embodying the invention.
Figure 2:
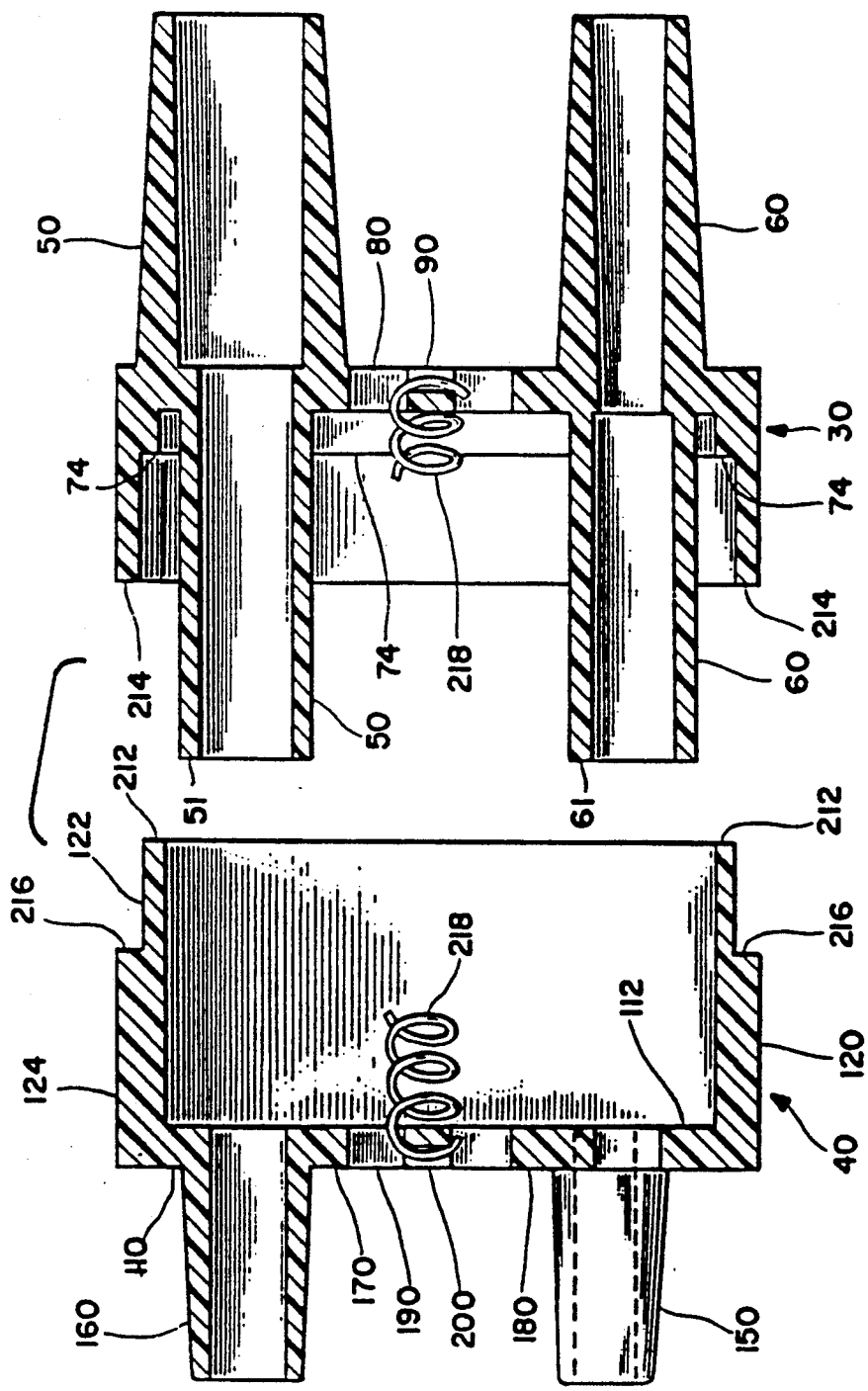
FIG. 2 is a sectional exploded view of the control valve shown in FIG. 1.
Figure 5:
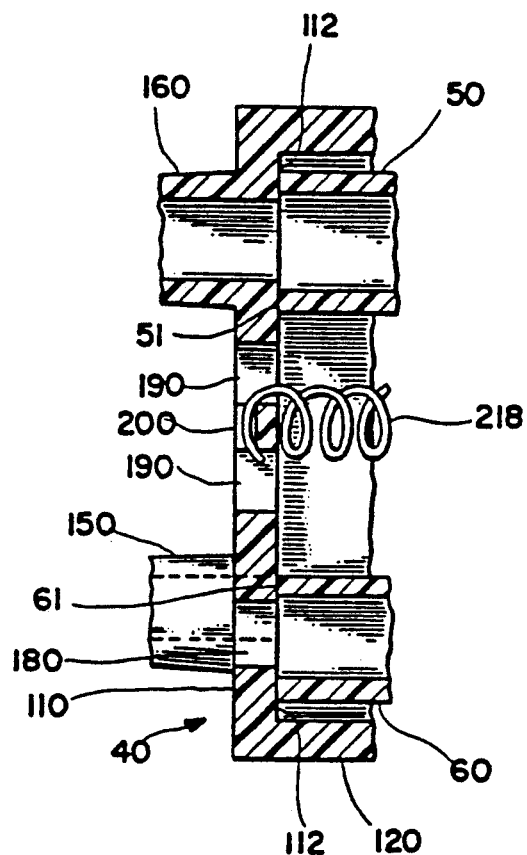
FIG. 5 is a sectional view of a portion of the control valve shown in Fig. and showing the relationship of certain parts when the of the invention control valve is assembled.
Figure 6:
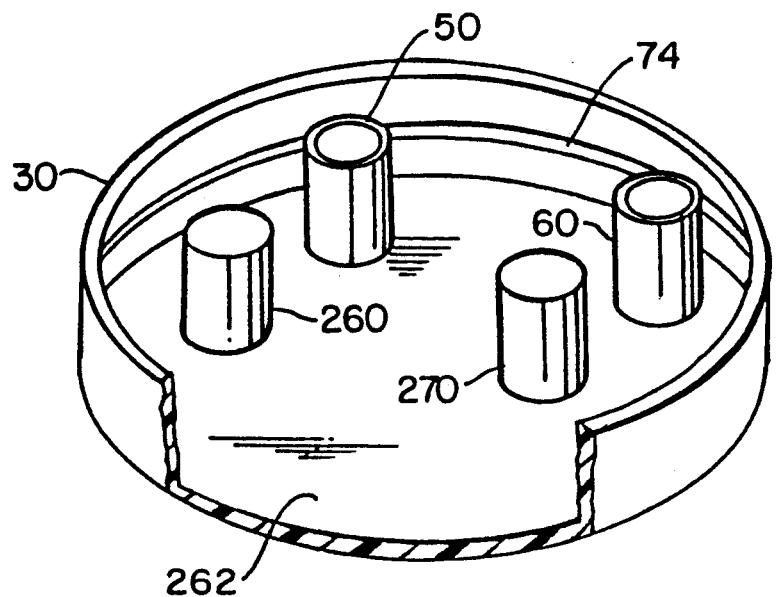
FIG. 6 is a perspective view of one portion of the control valve shown in FIG. 1.
Figure 7:
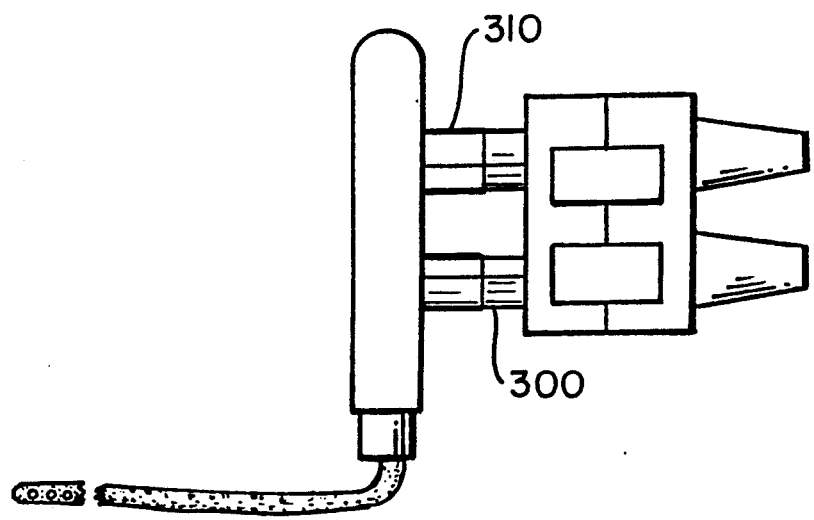
FIG. 7 is a plan view of the catheter system shown in FIG. 1.

The invention described herein includes a control valve for applying suction and oxygen separately to a patient. The invention comprises the combination of this control valve and a single small-diameter flexible tube through which oxygen and suction can be applied to a pediatric patient. The control valve includes some of the features of the valve described, and claimed in the subject inventor's U.S. Pat. No. 4,595,005 which is incorporated herein by reference.

Referring to the drawings and particularly to FIGS. 1 through 6 a dual purpose catheter system 10 embodying the invention includes a control valve 20 of a synthetic resinous material comprising two cylindrical bodies 30 and 40 rotatably coupled together. One body 30 includes a flat rear wall 44 through which first and second integral tubes 50 and 60 extend so that the two tubes lie inside and ouside the body 30 and thus inside the valve mechanism. The inner ends 51 and 61 of tubes 50 and 60 are as smooth as possible for a purpose to be described. Tube 50 is used for connection to a suction source and tube 60 for connection to an oxygen source and the suction tube 50 is preferably of larger diameter for identification purposes.

A portion 70 of the inner wall of body 30 ( FIG. 2) near wall 44 is thickened or is reduced in inside diameter to provide an annular ledge 74 which acts as a stop for the leading end of body 40 when the two bodies are assembled. The rear wall 44 of the body 30 also has a central hole 80 and a notched tab 90 which is formed integral with the body 30 and extends partly across the hole 80. The tab 90 has a notch or depression 92 in its outer surface.

An operating finger tab 100 extends generally perpendicularly from the outer surface of the body 30 for manipulation by the operator of the catheter system The lower edge of tab 100 has a notch 102 for a purpose to be described.

The second body 40 includes a rear wall 110, whose inner surface is as smooth as possible, for mating with other parts to be described. The annular outer wall 120 of body 40 has a portion 122 of reduced thickness, or of smaller outside diameter, at its leading end for insertion into body 30. Also, the outer surface of the thicker portion 124 is provided with a region 130 of reduced thickness (FIG. 1) having a ledge 123 (FIGS. 1 and 2) where it joins the portion 122 of reduced thickness. An integral operating finger tab 140 extends generally prpendicularly from the thicker annular wall portion at one end of the portion 130 of reduced thickness.

The finger tabs 100 and 140 are provided with roughened strips 142 on their outer opposite faces (FIGS. 2, 3 and 4) to facilitate their manipulation by the user of the system.

Two tubes 150 and 160 extend awazy from the wall 110, tube 150 for oxygen and tube 160 for suction. The two tubes 150 and 160 communicate with the inside of the body 40 through holes 152 and 162 in the rear wall 110. The tubes 150 and 160 are of different sizes and cross-section shapes to serve as keys or guides for coupling the valve to other apparatus to be described. The rear wall 110 also has two holes 170 and 180 located on the same circumference as the two tubes 150 and 160. The wall also has a central opening 190.

When the two bodies 30 and 40 are put together, the thin annular wall 122 of the body 40 fit snugly into the opening in body 30 and the leading end 212 butts up against the ledge 74. Similarly, the leading end 214 of body 30 butts up against ledge 216 where wall 122 meets wall 124 of the body 40. Also, the inner ends 51 and 61 of tubes 50 and 60 form a tight fit against the inner surface 112 of rear wall 110 of body 40 to provide an essentially leak-proof coupling between body 30 and body 40. When the bodies 30 and 40 are put together, the finger tab 100 slips over the rim 132 and the notch 102 in the lower surface thereof engages and locks on the rim.

The two bodies 30 and 40 are held together securely and tightly by means of a helical spring 218 which is secured at its ends in the notches 92 and 210 in the tabs 90 and 200. In attaching the spring 218, with the two bodies 30 and 40 loosely coupled together, one end of the spring is shaped like a hook and is secured to notch 92 and, with the other end grasped by a hooked tool, the spring is rotated to bias it, and then its other end, which is also shaped like a hook, is set in notch 210 in tab 200, ands the bodies are thus locked together. The spring holds bodies 30 and 40 tightly together with the inner portions 51 and 61 of tubes 50 and 60 snug against the inner surface 112 of end wall 110. The bias set into the spring serves to keep the bodies 30 and 40 rotated so that the finger tabs 100 and 140 are at their maximum distance aparet. With this orientation of the bodies, the oxygen tube 60 is aligned with the oxygen feed tube 150 through its hole 152 in wall 110 and the suction tube 50 is aligned with hole 170 and the ambient atmosphere. When the tabs 100 and 140 are squeezed together, the suction tube 50 is aligned with suction tube 160 through its hole 162 in the wall 110 and the oxygen tube 60 is aligned with the hole 180 to the ambient atmosphere.

The tube 50 is connected by flexible plastic tubing 220 to a source of suction (not shown) and the tube 60 is similarly connected by tubing 230 to an oxygen source (not shown).

In order to render the system 10 a closed system wherein the patient can be isolated from the valve 20 and cannot lose oxygen through the tubes 150 or 160, valve 20 is constructed so that the entrance openings inside the valve to rigid tubes 150 and 160 and to the patient are alternately blocked off from the patient as suction and oxygen are applied to the patient.

This is achieved by providing a first solid boss or cylinder 260 on the inner surface 262 of the wall of valve portion 30 and positioned just beneath the tube 60. A similar second solid boss or cylinder 270 is provided on the surface 262 just beneath the tube 50. The two bosses are of such a length, like tubes 50 and 60, that they contact and form a tight fit against the inner surface 112 of valve portion 40 when the two parts 30 and 40 of the valve 20 are assembled. The bosses 260 and 270 are positioned so that, when the source of oxygen is connected through tube 60, tube 150 and tube 240 to the patient and the suction tube is coupled to the opening to the atmosphere, boss 260 blocks the opening to tube 160 and to a lumen leading to the patient so that the patient cannot breathe into the valve through this lumen.

Similarly, when the suction lines are aligned and the patient is being suctioned, the source of oxygen is aligned with the opening to the atmosphere and the second boss 270 blocks the opening into tube 150 and to the lumen to the patient. Thus the patient cannot breathe into or from the valve 20 through the oxygen lumen and he cannotlose oxygen through valve 20.

In order to use the catheter system 10 as a pediatric catheter which requires a single, small diameter lumen or catheter tube for use with small children or infants whose bodies cannot accommodate a double lumen catheter. Thus, according to the invention, a coupling manifold 280 is provided to couple the two tubes 150 and 160 to a single small diameter tube or lumen 290. The coupling manifold 280 is tubular in form and is preferably made of a rigid synthetic resinous material. The manifold tube includes two short tubes 300 and 310 which are shaped and dimensioned so that tube 300 can engage valve tube 150 securely and the second tube can engage valve tube 160 securely.

The manifold tube 300 has one closed end 302 and an open end 304 to which the single lumen is secured. The single lumen has holes 320 at its remote end through which oxygen and suction can flow. As shown in FIG. 1, the suction tube 310 of the manifold is positioned oxygen tube 300 is positioned remote from the closed end of the manifold and closer to the open end 304 thereof. This arrangement permits the manifold to be cleaned of any mucus which might remain therein after a suctioning operation is performed on a patient. The application of suction with the apparatus removed from the patient clears the manifold of mucus.

It is noted that when the system 10 is used, the manifold tube 300 lies horizontally across the valve 20 so that the lumen 290 extends away from the manifold and valve. With the lumen 290 thus extending away and to the side of the valve, the user can sight more easily as he directs the lumen into the mouth of a child.

What is claimed is:

1. A dual purpose catheter assembly comprising
   valve means for supplying oxygen and suction to a patient, said valve means having first and second tube means, said first tube means being adapted to be connected to a source of oxygen and said second tube means being adapted to be connected to a source of suction,
   said valve means having third and fourth tube means adapted to be coupled to a patient, said first tube means being aligned with said third tube means so that said valve means can be operated to feed oxygen from said source of oxygen to said third tube means, said fourth tube means being aligned with said second tube means so that said valve can apply suction from said source of suction to said fourth tube means,
   rigid bosses inside said valve means positioned so that when said third tube means is coupled to a patient, one boss blocks said fourth tube means and when said fourth tube means is connected to a patient, the other boss blocks said third tube means,
   a tubular coupling manifold having a first input coupling tube coupled to said third tube means and a second input coupling tube coupled to said fourth tube means, said manifold having a single output means for coupling to a patient, and
   a tube assembly for coupling said manifold directly to a patient, said tube assembly consisting of a single small diameter tube of a diameter insertable into an infant coupled to said single output means of said coupling manifold,
   said single tube having a patient end which has a plurality of holes for providing suction or oxygen to a patient, said single tube transporting both oxygen and suction separately under the control of said valve means.

2. The apparatus defined in claim 1 wherein said coupling manifold is tubular in form and has a closed end and an open end which comprises said single output means, said single tube being coupled to said open end of said manifold.

3. The apparatus defined in claim 1 wherein said coupling manifold is oriented so that said single tube extends away from said valve means and can be readily aimed by the user of said apparatus.

4. A dual-purpose apparatus for a pulmonary catheter comprising
   a rigid valve mechanism including a patient end and a second end for applying oxygen and suction thereto,
   a suction tube connected to said second end of said valve mechanism for applying suction thereto,
   an oxygen tube connected to said second end of said valve mechanism for applying oxygen thereto,
   a patient oxygen tube coupled to said patient end of said valve mechanism,
   a patient suction tube coupled to said patient end of said valve mechanism,
   a coupling device having first and second coupling tubes for connection to said patient oxygen tube and said patient suction tube, said coupling device also having a single output tube coupled to a patient, said single output tube consisting of a single small diameter tube of a diameter insertable into an infant and said single output tube transporting both oxygen and suction separately under the control of said valve mechanism,
   an oxygen vent hole and a suction vent hole in said valve mechanism,
   a first blocking means in said valve mechanism,
   a second blocking means in said valve mechanism, and
   means for moving said second end of said valve mechanism with respect to said patient end thereof whereby:
   (1) said suction tube is coupled to said patient suction tube to apply suction to a patient, said oxygen tube is not coupled to said patient oxygen tube, said oxygen vent hole and said suction vent hole being open, and said first blocking means obstructs said patient oxygen tube which is thereby blocked from communication with a patient, (2) when said oxygen tube is coupled to said patient oxygen tube said suction tube is not coupled to said patient suction tube, said suction vent hole and said oxygen vent hole being open and said second blocking means obstructs said patient suction tube which is thereby blocked from communication with a patient.

5. The apparatus defined in claim 4 wherein said first and second blocking means comprise solid bosses disposed inside said valve mechanism, one adjacent to said suction tube and one adjacent to said oxygen tube.

6. The apparatus defined in claim 4 wherein said valve mechanism, said oxygen tube, said suction tube, said patient oxygen tube and said patient suction oxygen tube are of a rigid synthetic resinous material.

7. The apparatus defined in claim 4 wherein said valve mechanism comprises first and second cylindrical members coupled together for rotation with respect to each other.

8. The apparatus defined in claim 7 wherein said first cylindrical member includes a wall, having an inner surface and an outer surface, to which said suction tube and said oxygen tube are secured and said second cylindrical member includes a wall, having an inner surface and an outer surface, to which said patient suction tube and said patient oxygen tube are secured.

9. The apparatus defined in claim 8 wherein said suction tube and said oxygen tube extend from said wall of said first cylindrical member up to the inner surface of said wall of said second cylindrical member whereby said oxygen tube can be aligned with said patient oxygen tube and form a generally tight fit therewith and said suction tube can alternately be aligned with said patient suction tube and form a generally tight fit therewith.

10. The apparatus defined in claim 7 and including finger tabs secured to said first and second cylindrical members for rotating said first and second tubular members with respect to each other.

11. The apparatus defined in claim 7 wherein said bosses are secured to the inner surface of the wall of said first cylindrical member and they extend toward the inner surface of said wall of said second cylindrical member.

12. The apparatus defined in claim 4 wherein said coupling manifold consists of a tubular member having a closed end and an open end and said single tube is connected to sasid open end, said first coupling tube of said coupling manifold being coupled to said patient suction tube of said valve mechanism, said first coupling tube being formed on said coupling manifold so that it is positioned close to said closed end thereof whereby when suction is applied to said valve mechanism and to said coupling member, it removes mucus which might be trapped in said coupling manifold.

13. A dual purpose catheter assembly particularly for use with infants including a valve including (1) a first flow path having an inlet for receiving oxygen and an outlet for flowing oxygen to a patient and (2) a second flow path having an inlet for receiving suction and an outlet for suctioning a patient, there being two outlets on said valve, a manifold having two inlet tubes coupled to said two outlets on said valve, said manifold having a single outlet means, and a patient tube assembly coupled to said single outlet means on said manifold, said patient tube assembly consisting of a single flexible tube, said single flexible tube being insertable into the lungs of an infant, said single flexible tube transporting both oxygen and suction separately under the control of said valve.

14. The assembly defined in claim 13 wherein said manifold is generally tubular and is oriented on a horizontal axis so that said single flexible tube extends laterally from said assembly and is visible to the user of said assembly whereby said user can guide the single tube into a patient.

15. The assembly defined in claim 13 wherein said manifold is generally tubular in form and has a closed and and an open end which comprises aid single outlet means, said two inlet tubes of said manifold consisting of a first inlet for receiving oxygen and a second inlet tube for receiving suction, said second inlet tube being disposed close to said closed end of said manifold whereby suction can be applied thereto to completely remove mucus in said manifold after a suctioning operation has been performed on a patient.

* * * * *